US012691125B2

(12) United States Patent
Ko et al.

(10) Patent No.: US 12,691,125 B2
(45) Date of Patent: Jul. 28, 2026

(54) PREVENTION OF ESTRUS IN SOW AND RUMINANTS

(71) Applicant: Insigna Inc., Champaign, IL (US)

(72) Inventors: CheMyong Ko, Champaign, IL (US); ChanJin Park, Savoy, IL (US); Rex Allen Hess, Champaign, IL (US); Po-Ching Patrick Lin, Champaign, IL (US)

(73) Assignee: Insigna, Inc., Champaign, IL (US)

( * ) Notice: Subject to any disclaimer, the term of this patent is extended or adjusted under 35 U.S.C. 154(b) by 446 days.

(21) Appl. No.: 18/324,786

(22) Filed: May 26, 2023

(65) Prior Publication Data

US 2023/0381198 A1     Nov. 30, 2023

Related U.S. Application Data

(63) Continuation-in-part of application No. 17/937,740, filed on Oct. 3, 2022, now Pat. No. 11,938,140.

(60) Provisional application No. 63/378,226, filed on Oct. 3, 2022, provisional application No. 63/365,389, filed on May 26, 2022.

(51) Int. Cl.

| | |
|---|---|
| *C07J 1/00* | (2006.01) |
| *A61K 9/00* | (2006.01) |
| *A61K 31/565* | (2006.01) |
| *A61K 31/568* | (2006.01) |
| *A61P 5/26* | (2006.01) |
| *A61P 5/30* | (2006.01) |
| *A61P 15/00* | (2006.01) |

(52) U.S. Cl.
CPC .......... *A61K 31/565* (2013.01); *A61K 9/0019* (2013.01); *A61P 15/00* (2018.01)

(58) Field of Classification Search
CPC . C07J 1/00; A61K 9/00; A61K 31/565; A61K 31/568; A61P 5/26; A61P 5/30
See application file for complete search history.

(56) References Cited

U.S. PATENT DOCUMENTS

| | | | | |
|---|---|---|---|---|
| 3,991,750 | A | * 11/1976 | Vickery | A61K 9/1676 |
| | | | | 600/35 |
| 4,096,239 | A | 6/1978 | Katz et al. | |
| 4,123,519 | A | 10/1978 | Tribble et al. | |
| 4,210,644 | A | 7/1980 | Desjardins et al. | |
| 4,610,687 | A | 9/1986 | Fogwell | |
| 5,035,891 | A | 7/1991 | Runkel et al. | |
| 5,314,882 | A | 5/1994 | Pantic et al. | |
| 6,063,395 | A | 5/2000 | Markkula et al. | |
| 6,458,387 | B1 | 10/2002 | Scott et al. | |
| 7,589,082 | B2 | 9/2009 | Savoir et al. | |
| 11,135,229 | B2 | 10/2021 | Ko | |
| 11,938,140 | B2 | 3/2024 | Ko et al. | |
| 2011/0112475 | A1 | 5/2011 | Benson | |
| 2017/0258808 | A9 | 9/2017 | Yoakum et al. | |
| 2020/0171047 | A1 | 6/2020 | Ko | |
| 2020/0171048 | A1 | 6/2020 | Ko | |
| 2022/0370474 | A1 | 11/2022 | Ko | |
| 2023/0381197 | A1 | 11/2023 | Ko et al. | |
| 2023/0381199 | A1 | 11/2023 | Ko et al. | |
| 2023/0381200 | A1 | 11/2023 | Ko et al. | |
| 2024/0180926 | A1 | 6/2024 | Ko et al. | |
| 2026/0076978 | A1 | 3/2026 | Ko et al. | |

FOREIGN PATENT DOCUMENTS

| | | |
|---|---|---|
| CN | 113423391 A | 9/2021 |
| GB | 636908 A | 5/1950 |
| WO | WO-2020112180 A1 | 6/2020 |
| WO | 2023230607 | 11/2023 |
| WO | 2023230619 | 11/2023 |

(Continued)

OTHER PUBLICATIONS

"U.S. Appl. No. 16/526,874, 312 Amendment filed Jul. 8, 2021", 3 pgs.
"U.S. Appl. No. 16/526,874, Advisory Action mailed Sep. 9, 2020", 5 pgs.
"U.S. Appl. No. 16/526,874, Examiner Interview Summary mailed Jun. 1, 2021", 3 pgs.
"U.S. Appl. No. 16/526,874, Final Office Action mailed Apr. 26, 2021", 8 pgs.
"U.S. Appl. No. 16/526,874, Final Office Action mailed Jun. 9, 2020", 10 pgs.
"U.S. Appl. No. 16/526,874, Non Final Office Action mailed Nov. 24, 2020", 8 pgs.
"U.S. Appl. No. 16/526,874, Non Final Office Action mailed Dec. 11, 2019", 6 pgs.
"U.S. Appl. No. 16/526,874, Notice of Allowability mailed Aug. 30, 2021", 5 pgs.
"U.S. Appl. No. 16/526,874, Notice of Allowance mailed Jul. 2, 2021", 8 pgs.

(Continued)

*Primary Examiner* — Brenda L Coleman
(74) *Attorney, Agent, or Firm* — Schwegman Lundberg & Woessner, P.A.

(57) ABSTRACT

Embodiments of the present invention provide a pharmaceutical intervention in neonatal to infantile pigs, ruminants, and other livestock that inhibits the activation of the HPG axis, growth of the gonads and inhibits gonadal production of sex hormones, which will prevent the estrous cycle until the age at slaughter. The invention comprises treatment with estrogen or estrogen in combination with androgen in the newborn to infantile females using extended drug delivery methods, with a defined duration of between 1-4 months or infantile period of growth, for the purpose of the prevention of the estrous cycle in female production animals. The drug delivery component may consist of biocompatible polymers in the form of pellets, microspheres, or gels, or in solvents or solutions (hereafter, drug complex). The invention embodies neonatal to infantile period treatment with a drug complex consisting of a hormone-based compound configured to inhibit development and function of hypothalamic Kisspeptin neurons, pituitary release of luteinizing hormone/follicle stimulating hormone and postnatal development of the ovary through the use of sustained but temporary release of the compounds into the body of an animal once the drug-carrier has been injected or implanted therein.

13 Claims, 3 Drawing Sheets

(56)                    References Cited

FOREIGN PATENT DOCUMENTS

WO          2023230621          11/2023
WO          2024076995          4/2024

OTHER PUBLICATIONS

"U.S. Appl. No. 16/526,874, Response filed Feb. 16, 2021 to Non Final Office Action mailed Nov. 24, 2020", 7 pgs.
"U.S. Appl. No. 16/526,874, Response filed Mar. 10, 2020 to Non Final Office Action mailed Dec. 11, 2019", 7 pgs.
"U.S. Appl. No. 16/526,874, Response filed Jun. 9, 2021 to Final Office Action mailed Apr. 26, 2021", 7 pgs.
"U.S. Appl. No. 16/526,874, Response filed Aug. 17, 2020 to Final Office Action mailed Jun. 9, 2020", 8 pgs.
"U.S. Appl. No. 16/526,874, Response filed Oct. 9, 2020 to Advisory Action mailed Sep. 9, 2020", 10 pgs.
"U.S. Appl. No. 16/699,307, Final Office Action mailed Jan. 11, 2021", 12 pgs.
"U.S. Appl. No. 16/699,307, Non Final Office Action mailed May 12, 2020", 7 pgs.
"U.S. Appl. No. 16/699,307, Non Final Office Action mailed Jun. 28, 2021", 16 pgs.
"U.S. Appl. No. 16/699,307, Response filed Apr. 12, 2021 to Final Office Action mailed Jan. 11, 2021", 11 pgs.
"U.S. Appl. No. 16/699,307, Response filed Nov. 12, 2020 to Non Final Office Action mailed May 12, 2020", 8 pgs.
"U.S. Appl. No. 17/646,207, Non Final Office Action mailed Mar. 30, 2023", 9 pgs.
"U.S. Appl. No. 17/646,207, Preliminary Amendment filed Aug. 15, 2022", 5 pgs.
"U.S. Appl. No. 17/937,740, Final Office Action mailed Oct. 30, 2023", 6 pgs.
"U.S. Appl. No. 17/937,740, Non Final Office Action mailed Jul. 28, 2023", 5 pgs.
"U.S. Appl. No. 17/937,740, Response filed Oct. 13, 2023 to Non Final Office Action mailed Jul. 28, 2023", 5 pgs.
"U.S. Appl. No. 17/937,743, Final Office Action mailed Oct. 12, 2023", 17 pgs.
"U.S. Appl. No. 17/937,743, Non Final Office Action mailed Feb. 16, 2023".
"U.S. Appl. No. 17/937,743, Non Final Office Action mailed Jun. 8, 2023", 12 pgs.
"U.S. Appl. No. 17/937,743, Response filed Jan. 11, 2023 to Restriction Requirement mailed Jan. 5, 2023", 6 pgs.
"U.S. Appl. No. 17/937,743, Response filed May 16, 2023 to Non Final Office Action mailed Feb. 16, 2023", 6 pgs.
"U.S. Appl. No. 17/937,743, Response filed Sep. 8, 2023 to Non Final Office Action mailed Jun. 8, 2023", 10 pgs.
"U.S. Appl. No. 17/937,743, Restriction Requirement mailed Jan. 5, 2023".
"U.S. Appl. No. 18/099,654, Preliminary Amendment filed Apr. 10, 2023", 9 pgs.
"Chinese Application Serial No. 201980089378.4, Office Action mailed Apr. 12, 2023", w/English Translation, 11 pgs.
"Chinese Application Serial No. 201980089378.4, Office Action mailed Aug. 29, 2022", w/ English translation, 18 pgs.
"Chinese Application Serial No. 201980089378.4, Response Filed Jan. 13, 2023 to Office Action mailed Aug. 29, 2022", W/ English Claims, 13 pgs.
"Claims of copending U.S. Appl. No. 17/937,740", (Oct. 3, 2022), 2 pgs.
"European Application Serial No. 19891161.2, Extended European Search Report mailed Jul. 15, 2022", 9 pgs.
"European Application Serial No. 19891161.2, Response Filed Jan. 10, 2023 to Extended (European Search Report mailed Jul. 15, 2022", 10 pgs.
"Guide to the care and use of experimental animals", Canadian Council on Animal Care, p. 371, Atomic Energy Press, vol. 1, (1993), 300 pgs.

"International Application Serial No. PCT/US2019/044230, International Preliminary Report on Patentability mailed Jun. 10, 2021", 6 pgs.
"International Application Serial No. PCT/US2019/044230, International Search Report mailed Oct. 29, 2019", 2 pgs.
"International Application Serial No. PCT/US2019/044230, Written Opinion mailed Oct. 29, 2019", 4 pgs.
"International Application Serial No. PCT/US2023/067550, International Search Report mailed Aug. 10, 2023", 2 pgs.
"International Application Serial No. PCT/US2023/067550, Written Opinion mailed Aug. 10, 2023", 4 pgs.
"International Application Serial No. PCT/US2023/067565, International Search Report mailed Sep. 27, 2023", 4 pgs.
"International Application Serial No. PCT/US2023/067565, Written Opinion mailed Sep. 27, 2023", 4 pgs.
"International Application Serial No. PCT/US2023/067568, International Search Report mailed Sep. 29, 2023", 3 pgs.
"International Application Serial No. PCT/US2023/067568, Written Opinion mailed Sep. 29, 2023", 4 pgs.
Aldal, Inghild, et al., "Levels of androstenone and skatole and the occurrence of boar taint in fat from young boars", Livestock Production Science, 95(1), (2005), 121-129.
Andresen, Øystein, et al., "Boar taint related compounds: Androstenone/skatole/other substances", Acta Veterinaria Scandinavica, 48(Suppl 1):S5, (2006), 4 pgs.
Atanassova, N, et al., "Permanent Effects of Neonatal Estrogen Exposure in Rats on Reproductive Hormone Levels, Sertoli Cell Number, and the Efficiency of Spermatogenesis in Adulthood", Endocrinology, 140(11), (1999), 5364-5373.
At-Taras, Eeman E, et al., "Reducing Estrogen Synthesis in Developing Boars Increases Testis Size and Total Sperm Production", Journal of Andrology, 27(4), (2006), 552-559.
Berger, T, et al., "Increased testicular estradiol during the neonatal interval reduces Sertoli cell numbers", Anim Reprod Sci. 2018;189:146-51., (2018), 146-151.
Bonneau, Michel, et al., "An international study on the importance of androstenone and skatole for boar taint: I. Presentation of the programme and measurement of boar taint compounds with different analytical procedures", Meat Science, 54(3), (2000), 251-259.
Bonneau, Michel, et al., "Pros and Cons of Alternatives to Piglet Castration: Welfare, Boar Taint, and Other Meat Quality Traits", Animals, 9(11), 884, (2019), 12 pgs.
Candek-Potokar, Marjeta, et al., "Alternatives to surgical castration in pigs", Životnov'dni nauki, 52(5): 41-51, (2015), 13 pgs.
Cortes, ME, et al., "The Role of Kisspeptin in the Onset of Puberty and in the Ovulatory Mechanism: A Mini-review", J Pediatr Adolesc Gynecol., 28(5), (2015), 286-291.
D'Anglemont De Tassigny, Xavier, et al., "Hypogonadotropic hypogonadism in mice lacking a functional Kiss1 gene", PNAS, 105(25), (2007), 10714-10719.
Daxenberger, A, et al., "Suppression of androstenone in entire male pigs by anabolic preparations", Livestock Production Science, 69(2), (2001), 139-144.
Garcia-Regueiro, JA, et al., "Evaluation of the contribution of skatole, indole, androstenone and androstenols to boar-taint in back fat of pigs by HPLC and capillary gas chromatography (CGC)", Meat Science, 25(4),, (1989), 307-316.
Gettys, T. W, et al., "Suppression of LH secretion by oestradiol, dihydrotestosterone and trenbolone acetate in the acutely castrated bull", J Endocrinol., 100(1), (1984), 107-112.
Gorski, R A, "Modification of ovulatory mechanisms by postnatal administration of estrogen to the rat", American Journal of Physiology, vol. 205, No. 5, (1963), 842-844.
Grindflek, E, et al., "Revealing genetic relationships between compounds affecting boar taint and reproduction in pigs", Journal of Animal Science, 89(3), (2011), 680-92.
Hayashi, S, "Sterilization of Female Rats by Neonatal Placement of Estradiol Micropellets in Anterior Hypothalamus", Endocrinol. Japan, vol. 23, No. 1, (1976), 55-60.
Hess, Rex A, et al., "Estrogens and development of the rete testis, efferent ductules, epididymis and vas deferens", Differentiation 118, (2021), 41-71.

(56)                    References Cited

OTHER PUBLICATIONS

Kind, Fred A, et al., "Inhibition of sexual development in male and female rats treated with various steroids at the age of five days", Acta Endocrinogica vol. 49, No. 2, (Jun. 30, 1965), 193-206.

López-Bote, C, et al., "The reduction of boar taint in male pigs by neonatal testosterone administration", Meat Science, 22(3), (1988), 163-171.

López-Bote, C, et al., "Trenbolone Acetate Induced Changes in the Genital Tract of Male Pigs", Journal of Veterinary Medicine, Series B, 41(1-10), (1994), 42-48.

Minabe, Shiori, et al., "Long-Term Neonatal Estrogen Exposure Causes Irreversible Inhibition of LH Pulses by Suppressing Arcuate Kisspeptin Expression via Estrogen Receptors a and b in Female Rodents", Endocrinology, 158(9), (2017), 2918-2929.

Minabe, Shiori, "Neonatal Estrogen Causes Irreversible Male Infertility via Specific Suppressive Action on Hypothalamic Kiss1 Neurons", Endocrinology, 160(5), (2019), 1223-1233.

Novaira, Horacio J, et al., "Disrupted Kisspeptin Signaling in GnRH Neurons Leads to Hypogonadotrophic Hypogonadism", Mol Endocrinol, 28(2), (2014), 225-238.

Pantic, V., et al., "Testicular Structure and Serum Concentration of Gonadal Steroids in Male Pigs Neonatally Castrated or Treated with Estradiol and Progesterone", Bulletin de l'Academie Serbe des Sciences etdes Arts Classe des Sciences Naturelles et Mathematiques: Science Naturelles, vol. 25, pp. 57-72, (1984), 57-72.

Rasmussen, Martin, et al., "Regulation of Porcine Hepatic Cytochrome P450—Implication for Boar Taint", Comput Struct Biotechnol J., 11(19), (2014), 106-112.

Rosa-E-Silva, Alzira, et al., "Prepubertal Administration of Estradiol Valerate Disrupts Cyclicity and Leads to Cystic Ovarian Morphology during Adult Life in the Rat: Role of Sympathetic Innervation", Endocrinology, 144(10), (2003), 4289-4297.

Sheridan, PJ, et al., "The effect of anabolic agents on growth rate and reproductive organs of pigs", Livestock Production Science, 26(4), (1990), 263-275.

Stewart, Lawton, "Implanting Beef Cattle", UGA Cooperative Extension Bulletin 1302, (2013), 8 pgs.

Uenoyama, Yoshihisa, et al., "Central Mechanism Controlling Pubertal Onset in Mammals: A Triggering Role of Kisspeptin", Front Endocrinol (Lausanne), 10:312, (2019), 12 pgs.

Ventanas, J, et al., "Testicular development, androstenone levels and androstenone odour of untreated and trenbolone implanted boars", Journal of the Science of Food and Agriculture, 57(1), (1991), 127-133.

Williamson, DE, et al., "A selective immunization procedure against 5a-androstenone in boars", Animal Science, 35(3), (1982), 353-360.

Zamaratskaia, G, et al., "Plasma skatole and androstenone levels in entire male pigs and relationship between boar taint compounds, sex steroids and thyroxine at various ages", Livestock Production Science, 87(2), (2007), 91-98.

"U.S. Appl. No. 17/937,740, Response filed Nov. 17, 2023 to Final Office Action mailed Oct. 30, 2023", 4 pgs.

"U.S. Appl. No. 17/937,740, Notice of Allowance mailed Dec. 6, 2023", 5 pgs.

"U.S. Appl. No. 17/937,740, 312 Amendment filed Dec. 12, 2023", 5 pgs.

"U.S. Appl. No. 17/937,740, PTO Response to Rule 312 Communication mailed Dec. 27, 2023", 2 pgs.

"U.S. Appl. No. 17/937,743, Response filed Jan. 3, 2024 to Final Office Action mailed Oct. 12, 2023", 7 pgs.

"International Application Serial No. PCT US2023 075842, Invitation to Pay Additional Fees mailed Jan. 23, 2024", 12 pgs.

"U.S. Appl. No. 17/937,743, Advisory Action mailed Jan. 19, 2024", 3 pgs.

"International Application Serial No. PCT US2023 075842, International Search Report mailed Mar. 15, 2024", 5 pgs.

"International Application Serial No. PCT US2023 075842, Written Opinion mailed Mar. 15, 2024", 11 pgs.

"U.S. Appl. No. 17/937,743, Non Final Office Action mailed Jul. 5, 2024", 25 pgs.

"U.S. Appl. No. 17/937,743, Response filed Dec. 5, 2024 to Non Final Office Action mailed Jul. 5, 2024", 9 pgs.

"International Application Serial No. PCT US2023 067550, International Preliminary Report on Patentability mailed Dec. 5, 2024", 6 pgs.

"International Application Serial No. PCT US2023 067568, International Preliminary Report on Patentability mailed Dec. 5, 2024", 6 pgs.

Rebourcet, Diane, "Sertoli Cells Maintain Leydig Cell Number and Peritubular Myoid Cell Activity in the Adult Mouse Testis", PLoS One, vol. 9, Issue 8, (2014), 13 pages.

U.S. Appl. No. 18/437,978, filed Feb. 9, 2024, Non-Surgical Prevention of Boar Taint and Aggressive Behavior.

"U.S. Appl. No. 17/937,743, Final Office Action mailed Mar. 19, 2025", 25 pgs.

"U.S. Appl. No. 18/324,798, Non Final Office Action mailed Nov. 17, 2025", 5 pgs.

"U.S. Appl. No. 18/437,978, Non Final Office Action mailed Nov. 17, 2025", 4 pgs.

"U.S. Appl. No. 19/334,213, Preliminary Amendment filed Dec. 8, 2025", 5 pgs.

"Brazilian Application Serial No. 1120240245314, Office Action mailed Mar. 9, 2025", w/ Machine English Translation, 2 pg.

"Brazilian Application Serial No. 1120240245314, Response Filed May 16, 2025 to Office Action mailed Mar. 9, 2025", w/ Machine English Translation, 11 pgs.

"International Application Serial No. PCT/US2023/067565, International Preliminary Report on Patentability mailed Dec. 5, 2024", 6 pgs.

"International Application Serial No. PCT/US2023/075842, International Preliminary Report on Patentability mailed Apr. 17, 2025", 13 pgs.

"Korean Application Serial No. 10-2024-7042762, Notice of Preliminary Rejection mailed Dec. 27, 2024", w/ English Translation, 6 pgs.

"Korean Application Serial No. 10-2024-7042763, Office Action mailed Dec. 27, 2024", w/ English Translation, 6 pgs.

"U.S. Appl. No. 18/437,978, Response filed Feb. 16, 2026 to Non Final Office Action mailed Nov. 17, 2025", 8 pgs.

"U.S. Appl. No. 18/324,798, Response filed Feb. 16, 2026 to Non Final Office Action mailed Nov. 17, 2025", 5 pgs.

"European Application Serial No. 23812819.3, Extended European Search Report mailed Feb. 25, 2026", 10 pgs.

"European Application Serial No. 23812820.1, Extended European Search Report mailed Feb. 25, 2026", 11 pgs.

Allrich, R. D, "Symposium Estrus, New Devices, and Monitoring Endocrine and Neural Control of Estrus In Dairy Cows 1", [Online]. Retrieved from the InternetURL http dx.doi.org https doi. org 10.3168 jds. S0022-03029477216-7, Sep. 1, 1994, 2738-2744.

Habert, "Effets des estrogenes sur le développement du testicule pendant la vie foetale et neonatale", Gynecologie Obstetrique and Fertilite, Elsevier Masson, FR, vol. 34, No. 10, With Machine English Translation, Oct. 1, 2006, 16 pgs.

Heitzman, R J, "The Effectiveness of Anabolic Agents in Increasing Rate of Growth in Farm Animals Report on Experiments in Cattle", Environmental Quality And Safety. Supplement, Thieme, Stuttgart, DE, No. 5, Jan. 1, 1976, 10 pgs.

Reynolds, "The effect of trenbolone acetate on the bovine oestrous cycle", Animal Reproduction Science., vol. 4, No. 2 URL https www.sciencedirect.com science article abs pii 0378432081900373, Oct. 1, 1981, 10 pages.

* cited by examiner

PREVENTION OF ESTRUS IN SOW AND RUMINANTS

CROSS-REFERENCE TO RELATED APPLICATIONS

This application claims priority and the benefit of U.S. application Ser. No. 17/937,740, filed Oct. 3, 2022 and U.S. Provisional Appl. Ser. Nos. 63/365,389 and 63/378,226, filed May 26, 2022 and Oct. 3, 2022, respectively, which are incorporated by reference as if fully set forth herein.

BACKGROUND

Raising animals to their maximum weight within a minimal period of time is of utmost importance to maximize profit in the production animal industry. However, when females reach puberty, and even before, their food intake and growth rates are decreased. This is a major cause of diminishing financial returns in female animals at slaughter.

Generally, young female pigs (gilts)(genus *Sus*) develop estrus around 140-185 days of age (1), which coincides with the window for slaughter. The frequency of estrus/heat is every 18-24 days, and the estrus period is continued over 3 days (2). Patterson et al. (2010) divided gilts into early puberty (first estrus <153 days of age), intermediate puberty (first estrus 154 to 167 days of age, and late puberty (first estrus 168 to 180 days of age) groups. The age of puberty onset affects bodyweight (BW). The BW, measured at multiple time points between 120-170 days, was significantly lighter in sows with early estrus than sows that experienced late puberty (1).

Goats (genus *Capra*) are often slaughtered as early as 3-5 months of age, but typically not later than 1-year-old. Goats typically go into estrus, or heat, every 18-24 days. The duration of estrus is approximately 24 to 36 hours (3). According to USDA, the meat from female goats (doe) is more desirable for steaks and chops because it is more tender than meat from the males (4). Female lambs (ewes)(genus *Ovis*) are often slaughtered between 6-8 months of age (5), typically after they have reached puberty (5.5-8.5 months) (6, 7, 8). The estrous cycle in ewes lasts approximately 13-19 days, with an average of about 17 days. The actual estrus period lasts from 24 to 36 hours (9). Cows (genus *Bos*) generally reach puberty at 1 year of age, and they are often slaughtered at 2.5-3.5 years of age (10). In cattle, the estrous cycle lasts approximately 21 days on average, but can range from 18 to 24 days. The estrus period typically lasts between 12 to 18 hours (9). Together, this indicates that female ruminants raised for meat production experience pubertal onset and first estrus during or before they reach slaughtering age.

Female ruminant meat increases the likelihood of consumers being exposed to animal-derived estrogen. In one species of cow (*Bos fronlalis*), the mean highest peak concentrations of E2 was 27.29 pg/ml and total estrogens was 45.69 pg/ml during the peri-estrus period (11). In humans, prepubertal girls and boys have estradiol levels of 1.6 pg/ml and 0.4 pg/ml on average, respectively. Thus, eating large amounts of meat derived from female livestock may expose prepubertal children to excessive sex steroids. Moreover, raising females for meat consumption represents a loss of profit for producers due to the decrease in feed efficiency after puberty. Unlike castrations in males, removal of the ovary requires a complicated and expensive surgery. Thus, surgical removal of the ovary is not an option for preventing the estrous cycle in meat production animals.

Exogenous hormones can imitate the hormones that regulate the natural estrous cycle in cattle, enabling producers to manipulate and synchronize estrus in cows and heifers, as well as reduce the length of their cycles. Presently, the use of immunization against gonadotropin-releasing hormone (GnRH) as an alternative to surgical removal of ovaries in production animals is being considered (12, 13). FDA-approved drugs in the gonadorelin class mimic the action of gonadotropin-releasing hormone (GnRH), which is naturally produced by the hypothalamus during the estrous cycle. They mimic the surge of GnRH that occurs just before ovulation, triggering the pituitary gland to release follicle-stimulating hormone (FSH) and luteinizing hormone (LH). FSH prompts the growth of new ovarian follicles, while LH leads to the rupture of the dominant follicle and egg release, thus causing ovulation. However, this method requires repeated treatments of animals before they reach puberty, which raises concerns regarding worker safety and increased cost of management.

Progestin-class drugs behave like the hormone progesterone, which is naturally secreted by the corpus luteum. These drugs can enhance the progesterone level in a cow or heifer to influence the release of FSH and LH from the pituitary gland, suppress estrus, and prevent ovulation. Although this allows controlling the estrous cycle, hence enhancing overall productivity, it necessitates additional labor and incurs further costs for treatment.

SUMMARY

One embodiment provides a method for inhibiting ovary development and function in ruminants, which prevents the pubertal rise in blood and tissue estrogen and the beginning estrous cycle, comprising injecting said ruminant animals with a combination of an estrogen or estrogen plus androgen within the early neonatal to beginning infantile period after birth of said ruminants for extended release during the neonatal/infantile period of growth. In one embodiment, the injection is either subcutaneous or intra-muscular. In one embodiment, the injection includes nasal inhalation.

One embodiment further comprises an implant, wherein the implant comprises said estrogen or estrogen plus androgen, wherein the estrogen and androgen target the hypothalamus-pituitary-ovary axis.

In one embodiment, the implant comprises a material or enclosure that maintains elevated circulating levels of compounds over the neonatal/infantile period. In one embodiment, the material or enclosure that provides sustained release consists of biodegradable polymers or biocompatible materials. In one embodiment, the material or enclosure that provides sustained release is a form of capsule, pellets, microspheres, gel, or solution.

In another embodiment, the injected estrogen and/or androgen are not present in the blood or tissues when the animals are slaughtered.

In one embodiment, the estrogen comprises natural or synthetic estrogenic compounds including estradiol esters such as estradiol benzoate (EB), estradiol valerate, estradiol cypionate, etc. In one embodiment, there is a dose range of 0.1-2 mg/kg BW.

In another embodiment, the androgen comprises testosterone, testosterone esters, androstenedione, trenbolone, trenbolone esters, 5α-dihydrotestosterone, 5α-dihydrotestosterone esters, synthetic androgens that has androgenic activity, or equivalents. In one embodiment, there is a dose range of 1-20 mg/kg BW.

One embodiment provides that the injected amount of the estrogen or estrogen plus androgen is in a dose sufficient to inhibit the development of Kisspeptin neurons in the hypothalamus, FSH/LH production in the pituitary, postnatal ovary development, ovarian steroidogenesis, estrous cycle, and ovulation.

BRIEF DESCRIPTION OF THE DRAWINGS

The drawings illustrate generally, by way of example but not by way of limitation, various embodiments discussed in the present document. In the drawings, which are not necessarily drawn to scale, like numerals may describe similar components in different views. Like numerals having different letter suffixes may represent different instances of similar components.

DETAILED DESCRIPTION

Figure 1:
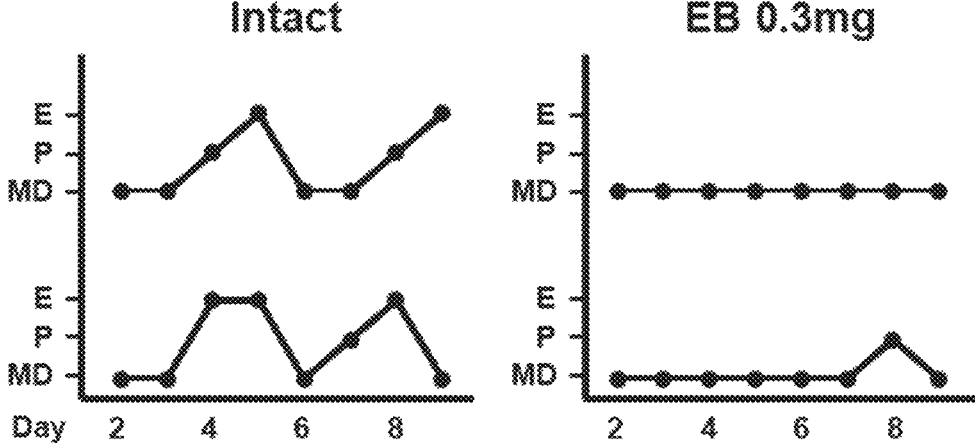
FIG. 1 illustrates exemplary estrous cycle from two subject groups (intact, EB 0.3 mg) in female rats at 2-3 months of age.

The following detailed description includes references to the accompanying drawings, which form a part of the detailed description. The drawings show, by way of illustration, specific embodiments in which the invention may be practiced. These embodiments, which may also be referred to herein as "examples," are described in enough detail to enable those skilled in the art to practice the invention. The example embodiments may be combined, other embodiments may be used, or structural, and logical changes may be made without departing from the scope of the present invention. While the disclosed subject matter will be described in conjunction with the enumerated claims, it will be understood that the exemplified subject matter is not intended to limit the claims to the disclosed subject matter. The following detailed description is, therefore, not to be taken in a limiting sense, and the scope of the present invention is defined by the appended claims and their equivalents.

In this document, the terms "a" or "an" are used to include one or more than one and the term; "or" is used to refer to a nonexclusive "or" unless otherwise indicated. In addition, the phraseology or terminology employed herein and not otherwise defined is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document, for irreconcilable inconsistencies, the usage in this document controls.

References in the specification to "one embodiment," "an embodiment," "an example embodiment," etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range but also to include all the individual numerical values or sub-ranges encompassed within that range as if each numerical value and sub-range is explicitly recited. For example, a concentration range of "about 0.1% to about 5%" should be interpreted to include not only the explicitly recited concentration of about 0.1 wt. % to about 5 wt. %, but also the individual concentrations (e.g., 1%, 2%, 3%, and 4%) and the sub-ranges (e.g., 0.1% to 0.5%, 1.1% to 2.2%, and 3.3% to 4.4%) within the indicated range.

The term "about" as used herein can allow for a degree of variability in a value or range—for example, within 10%, within 5%, within 1%, within 0.5%, within 0.1%, within 0.05%, within 0.01%, within 0.005%, or within 0.001% of a stated value or of a stated limit of a range—and includes the exact stated value or range.

As used herein, a "subject" is ruminant animals for production purposes. Ruminants include farm animals such as cattle, sheep, goats, deer, antelope, and camels. In other embodiments, similar approaches can be used for pig, llamas, horses, and other livestock.

The term "infertility" or "sterility" refers to the state of not being fertile or not being able to conceive offspring. Infertility may occur in either the male or the female or both.

The term "Sterilant" refers to compounds and a structure that delivers compounds in animals that induce permanent infertility, which is distinct from "contraceptive" that induces temporary infertility.

The term "estrous cycle" refers to the recurring reproductive cycle in female mammals, including estrus, ovulation, and changes in the uterine lining.

As used herein, an "effective amount" means an amount sufficient to prevent the onset of puberty, estrous cycle, or fertility. An effective amount can be administered in one or more administration. In some embodiments, an effective amount of estrogen alone or estrogen plus androgen can be achieved in conjunction with another drug, compound, or pharmaceutical composition. In other embodiments, an effective amount of estrogen alone or estrogen plus androgen may be achieved in isolation from the use of another drug, compound, or pharmaceutical composition.

The terms "carrier," "pharmaceutically acceptable carrier," or "physiologically acceptable carrier" as used herein refer to one or more formulation materials suitable for accomplishing or enhancing the delivery of estrogen alone or estrogen plus androgen as a composition (i.e., pharmaceutical composition).

Compositions and Methods

Described herein are compositions that comprise estrogen and androgen, and methods to use them to prevent an estrous cycle and fertility in ruminants. Other compounds that may be used in the methods described include, but are not limited to, estradiol, EB, estradiol dipropionate, estradiol valerate, estradiol cypionate (such that any form of chemical compound that releases estradiol or functionally acts like estradiol in vivo may be used), testosterone (T), testosterone esters, androstenedione, trenbolone (TB), trenbolone esters such as trenbolone acetate (TBA), 5α-dihydrotestosterone (DHT), 5α-dihydrotestosterone esters (such that any form of chemical compound that releases androgenic compounds or functionally acts like androgen in vivo may be used).

The invention is centered around a pharmaceutical intervention that inhibits the development of the gonads. In mammals, the reproductive process is regulated by hormones that are released from the Hypothalamus in the brain, the nearby Pituitary gland, and the distant Gonads that must be exposed to pituitary hormones via blood circulation. This physiological system is known as the HPG axis. In this system, a hormone produced in one region of the HPG axis either stimulates or inhibits the secretion of a hormone in another organ through a regulatory loop, respectively known as positive and negative feedback loops. Hypothalamic neurons produce two key reproductive hormones, Kisspeptin (KISS1) and GnRH (Gonadotropin-Releasing Hormone) (14, 15, 16, 17). In a unidirectional regulation, KISS1 is secreted, binds to the KISS1 receptor (GPR54) on the cell membrane of the GnRH neurons, triggering the release of GnRH. Notably, if either the Kiss1 or Gpr54 genes are removed, it results in hypogonadism and sterility (18, 19). GnRH travels to the pituitary via a local portal vein and triggers the secretion of LH (Luteinizing Hormone) and FSH (Follicle-Stimulating Hormone). Collectively, these peptide hormones stimulate the gonads to grow and produce sex steroids, primarily estrogen and androgen, as well as promote the production and release of germ cells.

In the hypothalamus, the target is the neuropeptide KISS1 produced by Kisspeptin neurons. This peptide initiates puberty by directly stimulating the release of GnRH (20, 21, 22). Therefore, KISS1 plays a crucial role in the facilitation of appropriate timing of puberty and normal gonadal development. Knockout of either the Kiss1 gene, which codes for KISS1, or its receptor, GPR54 on the GnRH neurons, was found to result in sterility in both male and female mice (19, 23, 24, 25, 26, 27). In female mouse, the loss of GPR54 provided direct evidence that the KISS1/GnRH neuron pathway regulates the onset of puberty. These mice displayed signs of sexual immaturity, irregular or no estrus cycles, underdeveloped gonads, low levels of sex steroids, and impaired ovulation (23, 24, 25).

Kisspeptin is expressed primarily in two regions of the hypothalamus, the preoptic area (POA) and the arcuate nucleus (ARC). Kisspeptin neurons in the POA are thought to be crucial for LH surges in females. On the other hand, Kisspeptin neurons in the arcuate nucleus mediate negative feedback effects of steroids on GnRH release in both adult males and females. Although Kisspeptin has an essential role initiating puberty in prepubertal mammals, it is still unclear how much the specific groups of Kisspeptin neurons, whether originating from the ARC or POA, contribute to this pathway.

The development of Kisspeptin neurons and the expression of KISS1 differs between the POA and the ARC. In the POA, Kiss1-expressing cells appear between postnatal days (PND) 8-10 in both male and female laboratory animals (mice and rats). Sexual dimorphism becomes evident around PND 10-12, as females show more Kisspeptin cells in the POA than do males. In contrast, KISS1 expression in the ARC begins during embryonic development. In both sexes, messenger RNA (mRNA) and protein expression appear around embryonic day 14.5, increasing through embryonic day 18.5, and declining just before birth at PND 0. ARC Kiss1 mRNA is detected at PND 0 as early as 0-4 hours after birth (28). Unlike the POA, arcuate Kiss1 is typically expressed during the first ten days of life in rodents, which then drops during the third postnatal week but increases again during the peri-pubertal period (29).

In further contrast to its expression in the POA, Kisspeptin expression in the ARC is compatible with the function of mediating negative feedback that occurs in both sexes. It has been found that ARC Kisspeptin expression appears to increase around the time of puberty onset in both sexes. In female rats, for example, both Kiss1 mRNA and neuron fiber density increase prior to pubertal onset, with increases occurring first in the ARC and later in the POA. This suggests that ARC Kisspeptin may be responsible for the onset of puberty (30).

Sex steroids appear to be necessary for proper development and organization of the Kisspeptin neurons, as well as for KISS1 expression. In Kisspeptin neuron-specific estrogen receptor-alpha (ESR 1) knockout mice, the number of Kisspeptin fibers in the hypothalamus was reduced (31). This is also true when hormones are depleted by gonadectomy in developing rodents. Estrogen and T inhibit Kiss1 expression in the ARC but increase Kiss1 expression in the POA (32). It has been found that Kisspeptin neurons colocalize with estrogen receptors (33) and, before puberty, estrogen signaling may repress Kisspeptin in the ARC, which could interrupt activation of the hypothalamic-pituitary-gonadal (HPG) axis, thereby preventing the premature onset of puberty.

Ovaries, the core organs of the female reproductive system, undergo dramatic developmental and structural changes from birth to puberty. Ovarian development produces four major cell types: 1) germ cells surrounded and nurtured by 2) granulosa cells, which with germ cells compose the follicles; 3) theca cells, surrounding follicles; 4) perifollicular myoid cells compose the outer layer of follicles.

In the female fetus, pituitary content of gonadotrophins and serum LH and FSH levels are higher than male fetuses during the first half of pregnancy (34, 35), and females have higher serum LH and FSH levels (35, 36, 37) than male fetuses. This sex difference has been suggested to be due to the negative feedback effects of fetal testicular hormones (38). However, LH and FSH levels decrease towards the end of gestation (34, 39), which is thought to result from the increased placental synthesis of estrogen and its negative feedback to HPG axis (38).

At birth, estrogen levels are low in both sexes (40, 41), but increase in females due to the ovarian follicular development and estrogen synthesis by granulosa cells (42). Postnatal HPG axis activation comprises transient elevation in circulating gonadotropins, LH and FSH, which occurs in the first weeks (rodents, cattle) or months (chimpanzees, humans) after birth in both males and females. In females, the circulating FSH level is more elevated than LH, while it is the opposite in males (43, 44, 45, 46, 47, 48). FSH induces estrogen synthesis and induces LH receptor expression in granulosa cells (49). The significant elevation of estrogen synthesis by ovarian follicles and LH receptor expression in granulosa cells are essential for pubertal onset and ovulatory function, respectively. Therefore, the most effective way to prevent the pubertal onset and estrous cycle, through the reduction of ovarian synthesis of estrogen and the inhibition of ovulation, is to inhibit neonatal development of the ovarian follicle.

Neonatal treatment of estrogen inhibits the primordial follicle formation in the neonatal mouse ovary in vivo, as well as in vitro (50). In the forming mouse ovary, oocytes develop as clusters of cells called nests or germ cell cysts. Shortly after birth, oocyte nests dissociate and granulosa cells surround individual oocytes forming primordial follicles. The treatment of neonatal females with estrogen inhibits the breakdown of the nests and primordial follicle assembly, both in organ culture and the live animal (50). This indicates that neonatal treatment with estrogen directly inhibits the neonatal follicle formation as well as prepubertal follicle development by disrupting the HPG axis.

In male mammals, there is a neonatal surge in testosterone, one of several significant increases that occur during their lifetime. However, this surge does not occur in the female (51). This post-birth testosterone surge in males is responsible for establishing male-specific sexual brain circuitry that controls sexually distinct behaviors and reproductive physiological functions (52). If the neonatal female is treated with an androgen, it defeminizes the brain and reproductive function (53). In the ovary treated neonatally with androgen, the pool of primordial follicle becomes abnormally small and the ovary displays disrupted ovulation when the animal matures (54). When mouse preantral follicles are treated with androgen in culture, the expression of CYP11A1 decreases. CYP11A1 is required for the initial stage of steroidogenesis (55), indicating that androgen treatment directly inhibits of ovarian steroidogenic function. Therefore, administering both estrogen and androgen to neonates provides synergy in inhibiting female reproductive differentiation. While giving estrogen to females may result in side effects like growth of uterine tissue, an androgen would counteract theses potential side effects (56). This suggests that a combination of estrogen and androgen can lead to a safe and effective prevention of the estrous cycle in females.

Currently, there are no non-surgical spaying techniques available that have a high degree of certainty for both disrupting Kisspeptin neuron development or KISS1 expression, with resultant decreases in LH/FSH production, as well as direct targeting of gonad development. The proposed invention provides a simple, easy-to-implement, pharmaceutical intervention in neonatal to infantile mammals that can replace the current use of surgical sterilization for preventing estrous cyclicity. A single injection of the two compounds (estrogen or estrogen+androgen) during the neonatal through infantile period, in a sustained-release carrier, will irreversibly inhibit the activation of the HPG axis in females, and inhibit the neonatal assembly and prepubertal development of ovarian follicles. Therefore, this treatment strategy will suppress the estrous cycle and sexual behavior in the female.

The drug pellet, microsphere, gel, or solution (hereafter, drug complex) comprises biocompatible polymers or solvents.

The drug complex comprises a hormone-based compound configured to inhibit the development of hypothalamic Kisspeptin neurons, postnatal release of LH/FSH from the pituitary and proliferation/maturation of cellular components in the gonads.

The drug complex allows for the sustained but temporary release of the steroids into a body of an animal once the drug-carrier has been injected or implanted therein.

Embodiments of the invention comprise insertion methods configured to allow injection of a drug complex through larger epidermal layers or muscle.

In some embodiments of the invention, the drug complex may comprise EB and EB plus TBA. In other embodiments, the drug complex may comprise other estrogen esters and other forms of androgens. In some embodiments, the drug complex is injected into the subject within the first week after birth to early infantile period depending on the species.

Embodiments of the invention may include farm animals, including pigs and ruminants such as cattle, sheep, goats, deer, antelope, camels, and other livestock while other embodiments of the invention may further include subjects physiologically similar to said subjects.

The invention involves the inhibition of gonad development and thereby the prevention of an estrous cycle by treating newborn mammals with a combination of a long-acting estrogen and an androgen in a delivery method that allows for sustained, but temporary elevation of the compounds through the weaning period (3 weeks after birth in rats). Estrogen alone, and the combined steroids, estrogen and androgen, permit the targeting of both the hypothalamus/pituitary region, as well as the gonads directly.

Concentration/Amount of Estrogen and/or Androgen

Sterilant (preventing the estrous cycle and inducing infertility) compositions comprise an infertility-inducing amount of estrogen and estrogen plus androgen. An effective amount of estrogen to prevent the estrous cycle can depend, for example, upon the route of administration, the age of the animal, and its size (i.e., BW). Accordingly, the skilled artisan may titer the dosage and modify the route of administration of estrogen to obtain the optimal effect for a particular animal.

In the case of the use of EB as estrogen, a typical dosage of EB may range from about 0.1 mg/kg to up to about 2 mg/kg or more. In other embodiments, the dosage of EB may range from 0.5 mg/kg up to about 2 mg/kg; or 1 mg/kg up to about 2 mg/kg; For example, in new born calf (30 kg bodyweight), 3, 15, 30 or 60 mg can be administered to induce infertility. In larger animals, a similar dose would be effective.

In the case of the use of TBA as an androgen, a typical dosage of androgen may range from about 1 mg/kg to up to about 20 mg/kg or more. In other embodiments, the dosage of androgen may range from 5 mg/kg up to about 20 mg/kg; or 10 mg/kg up to about 20 mg/kg; or 15 mg/kg up to about 20 mg/kg. For example, in new born calf (30 kg bodyweight), 30, 150, 450, or 600 mg can be administered to induce infertility. In larger animals, a similar dose would be effective.

Timing of Administration

Compositions comprising estrogen or estrogen in combination with androgen to prevent the estrous cycle are administered during the neonatal to infantile period prior to puberty (sexual maturity/capable of reproduction). The compositions can be administered days or weeks after birth depending on the species, as long as the compositions are administered during the neonatal/infantile period of growth. Administration of estrogen and estrogen plus androgen effectively inhibits/blocks maturation of sex organs/gonads.

Route of Administration

The route of administration of the composition provided herein is in accordance with known methods, e.g., injection (intraperitoneal, intramuscular, subcutaneous) and nasal (inhalation). In one embodiment, estrogen or estrogen in combination with androgen is administered for the prevention of the estrous cycle of an animal in a single, one-time dose. In other embodiments, multiple administrations of estrogen or estrogen in combination with androgen can be carried out to prevent the estrous cycle.

Compositions

In one embodiment, estrogen or estrogen in combination with androgen compositions for injectable administration can be in the form of oleaginous suspensions, including oil, such as vegetable oil (e.g., corn oil), cottonseed oil, peanut oil, and/or sesame oil. Other carriers or fillers can be used instead of, or in addition to, oil. Carriers/fillers can include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol. These suspensions can be formulated according to methods available to the art for dispersing and suspending ingredients.

In another embodiment, the composition described above can be encapsulated for administration. In one embodiment, a capsule can be formed from silicone tubing with plugs at each end to contain a mixture of, for example, estrogen, androgen and oil. The capsules can be placed, such as by injection (further described below), in the body of the subject. The estrogen and androgen compositions described herein can be formulated for immediate release or in a time release formulation (e.g., slow release). For example, estrogen and androgen can be prepared with carriers that protect estrogen and androgen against rapid release, such as a controlled release formulation.

Many methods for the preparation of controlled/slow-release formulations are known to those skilled in the art. For example, techniques for formulating a variety of sustained- or controlled-delivery means, such as liposome carriers, polymers (e.g., ethylene vinyl acetate, polyanhydrides, silicone, polyglycolic acid, collagen, polyorthoesters, poly-lactic acid and polylactic, polyglycolic copolymers (PLG), microparticles, nanoparticles (such as nanospheres, including biodegradable nanospheres or porous beads, and depot injections) are also known to those skilled in the art. For example, see PCT/US93/00829, which describes controlled release of porous polymeric microparticles for the delivery of pharmaceutical compositions. Additional examples of sustained-release preparations include semipermeable polymer matrices in the form of shaped articles, e.g., films or microcapsules. Sustained release matrices may include polyesters, hydrogels, polylactides (U.S. Pat. No. 3,773,919, EP 58,481), copolymers of L-glutamic acid and gamma ethyl-L-glutamate (51), poly (2-hydroxyethyl-methacrylate) (52, 53), ethylene vinyl acetate or poly-D(–)-3-hydroxybutyric acid (EP 133,988). Sustained-release compositions also include liposomes, which can be prepared by any of several methods known in the art. See e.g., Eppstein et al., (54), 1985; EP 36,676; EP 88,046; EP 143,949.

Controlled-release, slow release, or sustained release refer to the release of an active ingredient, such as estrogen and androgen, from a composition or dosage form in which the active ingredient is released over an extended period of time. In one embodiment, controlled-release results in dissolution over several hours to a few days or weeks. In another embodiment, APIs are released over a period of a few months, including about 1 to 4 months. In another embodiment, APIs are released over a neonatal/infantile period of growth.

In another embodiment, the composition is formulated for inhalation; for example, EB and TBA can be formulated as a dry powder. Inhalation solutions may also be formulated with a propellant for aerosol delivery. In another embodiment, inhalation solutions may be nebulized.

One embodiment provides kits for producing a single-dose administration unit. The kits may contain single and multi-chambered pre-filled syringes containing estrogen alone, estrogen plus androgen, and instructions for use (i.e., inhibiting gonad development, preventing the estrous cycle, or sterilizing an animal).

EXAMPLES

Example 1—Effects of Injecting Estrogen in Neonatal Rats Via Carrier on the Estrous Cycle Estradiol benzoate (Cat. #E8515, Sigma) was mixed with sesame oil (Cat. S3547, Sigma) and loaded into a Silastic™ tube (Cat. 508-005, Dow Corning) pre-cut to length (by the volume calculated from the inner diameter) to hold sufficient dose with an extra 1 mm on each end for sealing with medical silicone adhesive.

Neonates Sprague Dawley rats were divided randomly into two different groups: Control and Silastic capsule containing 0.3 mg EB in sesame oil (EB 0.3 mg), implanted on PND 0.5 (n=4). The injections and implants were placed on the back of the female rats in the nape area.

Determination of estrous cycle. Vaginal cytology performed daily in female rats from PND 62 to PND 69 to determine the estrous stage. For this, the tip of plastic pipette, filled with PBS or saline (~10 µL), was placed into the vagina. The vagina was flushed gently three to five times with same PBS/saline solution. Final flush was collected in pipette tip. A volume of 20 µL of saline solution containing vaginal cells moved to 96-well plate for observation of vaginal cytology. Unstained samples were observed under light microscope with a 10× objective. Metestrus/diestrus (MD), proestrus (P), and estrus (E) were defined from samples according to Westwood et al. (2008) (57).

Result. After the pubertal age, controls had normal estrous cycles, showed at least two estrus stages. However, EB 0.3 mg treated rats exhibited no sign of estrous cycle (FIG. 1). This indicates that neonatal treatment of EB disrupts the HPG axis which controls the estrous cycle in mammals even after the pubertal age.

Example 2—Effects of Injecting Estrogen in Neonatal Dogs Via Carrier on the Ovary Development Estradiol benzoate (Cat. #E8515, Sigma) was mixed with sesame oil (Cat. S3547, Sigma) and loaded into a Silastic™ tube (Cat. 508-005, Dow Corning) pre-cut to length (by the volume calculated from the inner diameter) to hold sufficient dose with an extra 1 mm on each end for sealing with medical silicone adhesive.

Neonates beagle dogs were divided randomly into two different groups: Intact and Silastic capsule containing 2 mg EB in sesame oil (EB 2 mg), implanted on PND 6 (n=3). The injections and implants were placed on the back of the dogs in the nape area.

Measurement of ovary volume. Ovary tissue were dissected from dogs at 3.5 months of age and oviduct was removed from the tissue to measure the ovary size. The size of ovary (length, width, and thickness) was measured using Vanier calipers. The volume ($mm^3$) was calculated by $2/3 \times$ the largest dimension of cross section ($mm^2$)×length (mm). Data is presented as mean±SD. The statistical difference between groups determined by Student's t-test.

Figure 2:
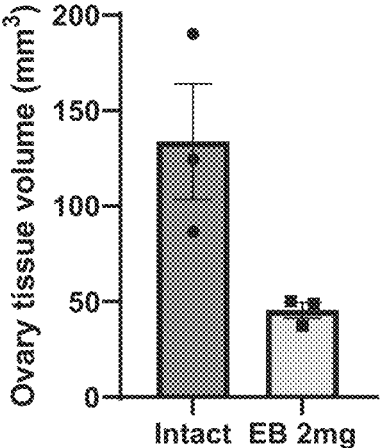
FIG. 2 illustrates exemplary ovary tissue volume data from three subject groups (intact, EB 2 mg) in beagle dogs at 3.5 months of age.

Result. The treatment of EB 2 mg in female neonatal beagle dogs at PND 6 resulted in 66% smaller ovary volume compared to those of intact dogs at 3.5 months of age (FIG. 2). The follicles of prepubertal ovary need FSH, which is secreted by pituitary, for their growth and survival (58, 59). However, the lack of KISS1 signal from the kisspeptin neurons causes the insufficient activation of pituitary gonadotrope cells, resulting in low FSH secretion (27). Collectively, insufficient ovary development in neonatally EB-treated beagle dogs indicates the impaired function of the HP axis.

Example 3—Effects of Injecting Estrogen and Androgen in Neonatal Pigs Via Carrier on the Ovary Development Treatment of animals. E2+TBA injectable implant contains E2 4 mg and TBA 20 mg (n=2) or E2 12 mg and TBA 60 mg (n=2) was implanted to neonatal female piglets (Large White X Landrace) on day 1 after birth by subcutaneous injection on the backside of the neck. The injection site of the implants was then sealed using the surgical sealant. Six untreated pigs served as an intact control group. All piglets were raised in the same pen until 8 weeks of age, ovary and uterus weight was measured at the end of the experiment. Data are presented using descriptive analysis as well as mean±SD of average testis weight in each individual. The ovarian tissues were fixed in 10% neutral formalin, embedded in paraffin, and then sectioned into 6 μm thick serial sections. Then, ovarian serial sections were stained with Hematoxylin and Eosin and observed under a microscope.

Figure 3:
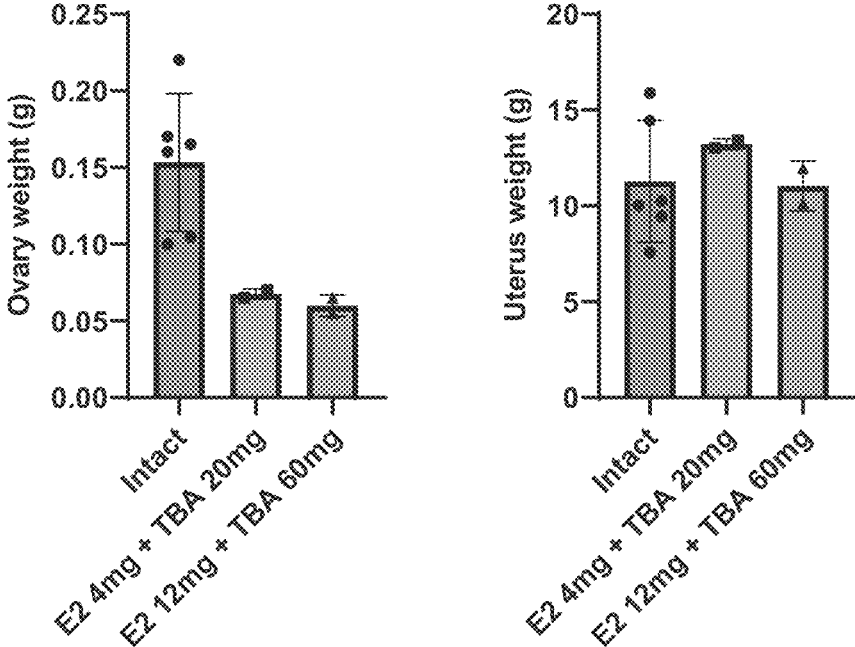
FIG. 3 illustrates exemplary ovary and uterus weight data from three subject groups (intact, E2 4 mg+TBA 20 mg, E2 12 mg+TBA 60 mg) in domestic pigs at 8 weeks of age.
Figure 4:
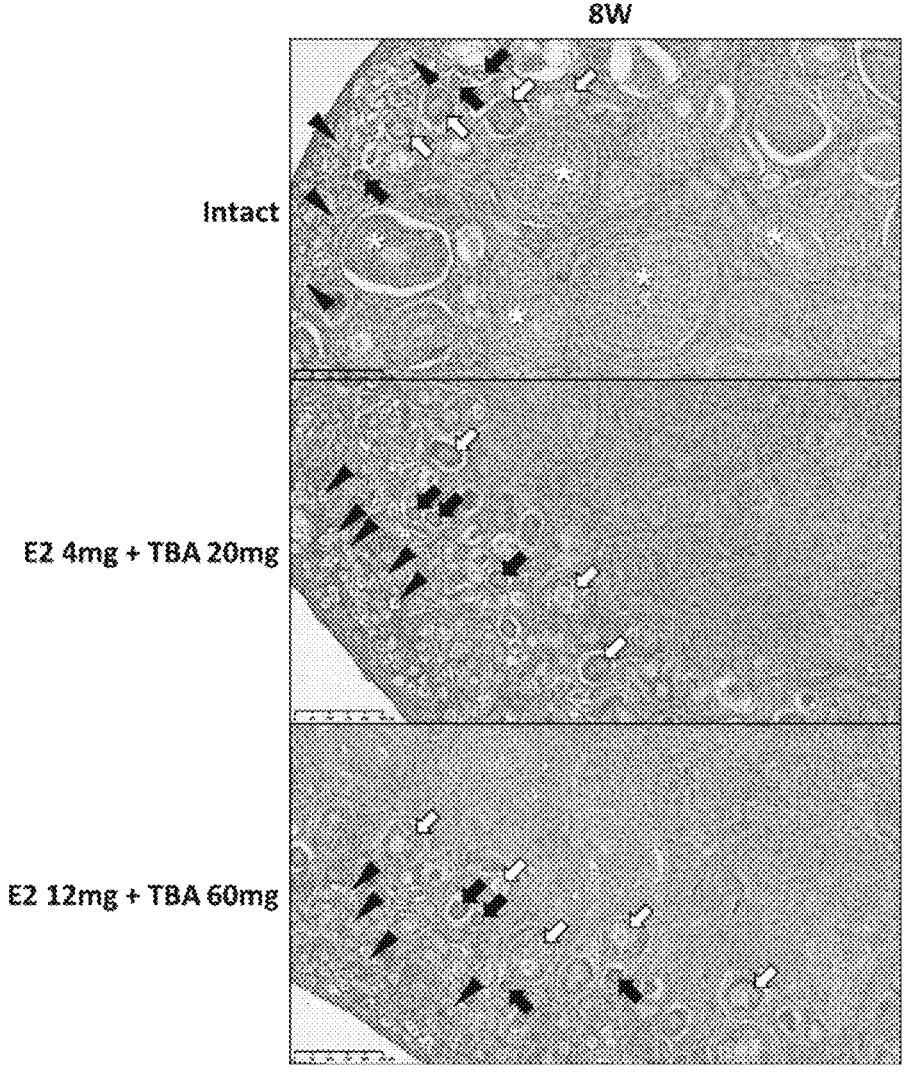
FIG. 4 illustrates exemplary ovary histology data from three subject groups (intact, E2 4 mg+TBA 20 mg, E2 12 mg+TBA 60 mg) in domestic pigs at 8 weeks of age. Arrow heads, primordial follicles; Black arrows, primary follicles; White arrows, secondary follicles; Asterisks, tertiary or advanced follicles.

Results. Control intact animals (n=3) showed 0.15±0.04 g ovary weight and 11.28±3.19 g uterus weight. Animals treated with E2 4 mg and TBA 20 mg had 56.0% lower ovary weight (0.07±0.00 g) than intact control. Animals treated with E2 8 mg and TBA 40 mg had 60.9% lower ovary weight (0.06±0.01 g) than control (FIG. 3). However, uterus weight was not different between groups. This indicates that neonatal treatment of EB+TBA inhibits the ovary but not uterine development in female pigs. Histological observations of the ovaries revealed the presence of numerous follicles, not only at the primordial, primary, and secondary stages, but also at the tertiary and beyond stages within the ovaries of the intact group. However, in pigs treated with EB+TBA, follicles at the tertiary stage or beyond were not present (FIG. 4). These results suggest that EB+TBA treatment inhibits the development of ovarian follicles, thereby suppressing hormone production and ovulation.

BIBLIOGRAPHY

1. Patterson J L, Beltranena E, Foxcroft G R. The effect of gilt age at first estrus and breeding on third estrus on sow body weight changes and long-term reproductive performance1. J Anim Sci. 2010; 88(7).2500-13.
2. Eliasson L. A study on puberty and oestrus in gilts. Zentralbl Veterinarmed A. 1989;36(1):46-54.
3. Smith M C, Sherman D M. Goat medicine: John Wiley & Sons; 2009.
4. USDA. Goat From Farm to Table 2013 [Available from: https://www.fsis.usda.gov/food-safety/safe-food-handling-and-preparation/meat/goat-farm-table.
5. USDA. Lamb From Farm to Table 2013 [Available from: https://www.fsis.usda.gov/food-safety/safe-food-handling-and-preparation/meat/lamb-farm-table.
6. Lozano H, Raes M, Vargas J J, Ballieu A, Grajales H, Manrique C, et al. Onset of puberty and regularity of oestral cycles in ewe lambs of four breeds under high-altitude conditions in a non-seasonal country. Trop Anim Health Prod. 2020; 52(6):3395-402.
7. Sakurai K, Ohkura S, Matsuyama S, Katoh K, Obara Y, Okamura H. Body growth and plasma concentrations of metabolites and metabolic hormones during the pubertal period in female Shiba goats. J Reprod Dev. 2004; 50(2): 197-205.
8. Amoah E, Bryant M. A note on the effect of contact with male goats on occurrence of puberty in female goat kids. Animal Science. 1984; 38(1):141-4.
9. Hafez E S E, Hafez B. Reproduction in farm animals: John Wiley & Sons; 2013.
10. Day M L, Nogueira G P. Management of age at puberty in beef heifers to optimize efficiency of beef production. Animal frontiers. 2013:3(4):6-11.
11. Mondal M, Rajkhowa C, Prakash B S. Relationship of plasma estradiol-17beta, total estrogen, and progesterone to estrus behavior in mithun (Bos frontalis) cows. Horm Behav. 2006; 49(5):626-33.
12. Di Martino G, Scollo A, Garbo A, Lega F, Stefani A L, Vascellari M, et al. Impact of sexual maturity on the welfare of immunocastrated v. entire heavy female pigs. Animal. 2018; 12(8):1631-7.
13. Delgadillo J A, De Santiago-Miramontes M A, Carrillo E. Season of birth modifies puberty in female and male goats raised under subtropical conditions. Animal. 2007; 1(6):858-64.
14. Tomikawa J, Homma T, Tajima S, Shibata T, Inamoto Y, Takase K, et al. Molecular characterization and estrogen regulation of hypothalamic KISS1 gene in the pig. Biology of reproduction. 2010; 82(2):313-9.
15. Scott C J, Rose J L, Gunn A J, McGrath B M. Kisspeptin and the regulation of the reproductive axis in domestic animals. J Endocrinol. 2019; 240:R1-R16.
16. Yeo S H, Colledge W H. The Role of Kiss1 Neurons As Integrators of Endocrine, Metabolic, and Environmental Factors in the Hypothalamic-Pituitary-Gonadal Axis. Front Endocrinol (Lausanne). 2018; 9:188.
17. Yeo S H, Kyle V, Blouet C, Jones S, Colledge W H. Mapping neuronal inputs to Kiss1 neurons in the arcuate nucleus of the mouse. PLoS One. 2019; 14(3):e0213927.
18. Novaira H J, Sonko M L, Hoffman G, Koo Y, Ko C, Wolfe A, et al. Disrupted kisspeptin signaling in GnRH neurons leads to hypogonadotrophic hypogonadism. Mol Endocrinol. 2014; 28(2):225-38.
19. d'Anglemont de Tassigny X, Fagg L A, Dixon J P, Day K, Leitch H G, Hendrick A G, et al. Hypogonadotropic hypogonadism in mice lacking a functional Kiss1 gene. Proceedings of the National Academy of Sciences of the United States of America. 2007; 104(25):10714-9.
20. Cortes M E, Carrera B, Rioseco H, Pablo del Rio J, Vigil P. The Role of Kisspeptin in the Onset of Puberty and in the Ovulatory Mechanism: A Mini-review. J Pediatr Adolesc Gynecol. 2015; 28(5):286-91.
21. Terasawa E, Guerriero K A, Plant T M. Kisspeptin and puberty in mammals. Adv Exp Med Biol. 2013; 784:253-73.
22. Uenoyama Y, Inoue N, Nakamura S, Tsukamura H. Central Mechanism Controlling Pubertal Onset in Mammals: A Triggering Role of Kisspeptin. Front Endocrinol (Lausanne). 2019; 10:312.
23. Seminara S B, Messager S, Chatzidaki E E, Thresher R R, Aciemo J S, Jr., Shagoury J K, et al. The GPR54 gene as a regulator of puberty. N Engl J Med. 2003; 349(17): 1614-27.

24. Messager S, Chatzidaki E E, Ma D, Hendrick A G, Zahn D, Dixon J, et al. Kisspeptin directly stimulates gonadotropin-releasing hormone release via G protein-coupled receptor 54. Proceedings of the National Academy of Sciences of the United States of America. 2005,102(5): 1761-6.

25. Funes S, Hedrick J A, Vassileva G, Markowitz L, Abbondanzo S, Golovko A, et al. The KiSS-1 receptor GPR54 is essential for the development of the murine reproductive system. Biochem Biophys Res Commun. 2003; 312(4):1357-63.

26. Ikegami K, Goto T, Nakamura S, Watanabe Y, Sugimoto A, Majarune S, et al. Conditional kisspeptin neuron-specific Kiss1 knockout with newly generated Kiss1-floxed and Kiss1-Cre mice replicates a hypogonadal phenotype of global Kiss1 knockout mice. J Reprod Dev. 2020, 66(4):359-67.

27. Lapatto R, Pallais J C, Zhang D, Chan Y M, Mahan A, Cerrato F, et al. Kiss1−/− mice exhibit more variable hypogonadism than Gpr54−/− mice. Endocrinology. 2007; 148(10):4927-36.

28. Semaan S J, Tolson K P, Kauffman A S. The development of kisspeptin circuits in the Mammalian brain. Adv Exp Med Biol. 2013; 784:221-52.

29. Takumi K, Iijima N, Ozawa H. Developmental changes in the expression of kisspeptin mRNA in rat hypothalamus. J Mol Neurosci. 2011; 43(2):138-45.

30. Coutinho E A, Esparza L A, Steffen P H, Bolleddu S, Kauffman A S. Dissecting the Involvement of Arcuate Nucleus Kisspeptin Neurons in Puberty Onset and LH Secretion. Journal of the Endocrine Society. 2021; 5(Supplement_1):A537-A.

31. Dubois S L, Acosta-Martinez M, DeJoseph M R, Wolfe A, Radovick S, Boehm U, et al. Positive, but not negative feedback actions of estradiol in adult female mice require estrogen receptor alpha in kisspeptin neurons. Endocrinology. 2015; 156(3):1111-20.

32. Kauffman A S. Sexual differentiation and the Kiss1 system: hormonal and developmental considerations. Peptides. 2009; 30(1):83-93.

33. Herber C B, Krause W C, Wang L, Bayrer J R, Li A, Schmitz M, et al. Estrogen signaling in arcuate Kiss1 neurons suppresses a sex-dependent female circuit promoting dense strong bones. Nat Commun. 2019; 10(1): 163.

34. Guimiot F, Chevrier L, Dreux S, Chevenne D, Caraty A, Delezoide A L, et al. Negative fetal FSH/LH regulation in late pregnancy is associated with declined kisspeptin/KISS1R expression in the tuberal hypothalamus. J Clin Endocrinol Metab. 2012; 97(12):E2221-9.

35. Kaplan S L, Grumbach M M. The ontogenesis of human foetal hormones. II. Luteinizing hormone (LH) and follicle stimulating hormone (FSH). Acta Endocrinol (Copenh). 1976; 81(4):808-29.

36. Clements J A, Reyes F I, Winter J S, Faiman C. Studies on human sexual development. III. Fetal pituitary and serum, and amniotic fluid concentrations of LH, CG, and FSH. J Clin Endocrinol Metab. 1976; 42(1):9-19.

37. Reyes F I, Winter J S, Faiman C. Studies on human sexual development. I. Fetal gonadal and adrenal sex steroids. J Clin Endocrinol Metab. 1973; 37(1):74-8.

38. Kuiri-Hanninen T, Sankilampi U, Dunkel L. Activation of the hypothalamic-pituitary-gonadal axis in infancy: minipuberty. Horm Res Paediatr. 2014; 82(2):73-80.

39. Takagi S, Yoshida T, Tsubata K, Ozaki H, Fujii T K, Nomura Y, et al. Sex differences in fetal gonadotropins and androgens. J Steroid Biochem. 1977; 8(5):609-20.

40. Winter J S, Hughes I A, Reyes F I, Faiman C. Pituitary-gonadal relations in infancy: 2. Patterns of serum gonadal steroid concentrations in man from birth to two years of age. J Clin Endocrinol Metab. 1976; 42(4):679-86.

41. Bidlingmaier F, Wagner-Barnack M, Butenandt O, Knorr D. Plasma estrogens in childhood and puberty under physiologic and pathologic conditions. Pediatr Res. 1973; 7(11):901-7.

42. Kuiri-Hanninen T, Haanpaa M, Turpeinen U, Hamalainen E, Seuri R, Tyrvainen E, et al. Postnatal ovarian activation has effects in estrogen target tissues in infant girls. J Clin Endocrinol Metab. 2013; 98(12):4709-16.

43. Winter J S, Faiman C, Hobson W C, Prasad A V, Reyes F I. Pituitary-gonadal relations in infancy. I. Patterns of serum gonadotropin concentrations from birth to four years of age in man and chimpanzee. J Clin Endocrinol Metab. 1975; 40(4):545-51.

44. Dohler K D, Wuttke W. Changes with age in levels of serum gonadotropins, prolactin and gonadal steroids in prepubertal male and female rats. Endocrinology. 1975; 97(4):898-907.

45. Rawlings N C, Evans A C, Honaramooz A, Bartlewski P M. Antral follicle growth and endocrine changes in prepubertal cattle, sheep and goats. Anim Reprod Sci. 2003; 78(3-4):259-70.

46. Bergada I, Milani C, Bedecarras P, Andreone L, Ropelato M G, Gottlieb S, et al. Time course of the serum gonadotropin surge, inhibins, and anti-Mullerian hormone in normal newborn males during the first month of life. J Clin Endocrinol Metab. 2006; 91(10):4092-8.

47. Chellakooty M, Schmidt I M, Haavisto A M, Boisen K A, Damgaard I N, Mau C, et al. Inhibin A, inhibin B, follicle-stimulating hormone, luteinizing hormone, estradiol, and sex hormone-binding globulin levels in 473 healthy infant girls. J Clin Endocrinol Metab. 2003; 88(8):3515-20.

48. Dullaart J, Kent J, Ryle M. Serum gonadotrophin concentrations in infantile female mice. J Reprod Fertil. 1975; 43(1):189-92.

49. Francois C M, Petit F, Giton F, Gougeon A, Ravel C, Magre S, et al. A novel action of follicle-stimulating hormone in the ovary promotes estradiol production without inducing excessive follicular growth before puberty. Sci Rep. 2017; 7:46222.

50. Chen Y, Jefferson W N, Newbold R R, Padilla-Banks E, Pepling M E. Estradiol, progesterone, and genistein inhibit oocyte nest breakdown and primordial follicle assembly in the neonatal mouse ovary in vitro and in vivo. Endocrinology. 2007; 148(8):3580-90.

51. Clarkson J, Herbison A E. Hypothalamic control of the male neonatal testosterone surge. Philos Trans R Soc Lond B Biol Sci. 2016; 371(1688):20150115.

52. Lenz K M, McCarthy M M. Organized for sex—steroid hormones and the developing hypothalamus. Eur J Neurosci. 2010; 32(12):2096-104.

53. Bloch G J, Mills R. Prepubertal testosterone treatment of neonatally gonadectomized male rats: defeminization and masculinization of behavioral and endocrine function in adulthood. Neurosci Biobehav Rev. 1995; 19(2):187-200.

54. Tyndall V, Broyde M, Sharpe R, Welsh M, Drake A J, McNeilly A S. Effect of androgen treatment during foetal and/or neonatal life on ovarian function in prepubertal and adult rats. Reproduction. 2012; 143(1):21-33.

55. Laird M, Thomson K, Fenwick M, Mora J, Franks S, Hardy K. Androgen Stimulates Growth of Mouse Preantral Follicles In Vitro: Interaction With Follicle-Stimulating Hormone and With Growth Factors of the TGFbeta Superfamily. Endocrinology. 2017; 158(4):920-35.

56. Hung T T, Gibbons W E. Evaluation of androgen antagonism of estrogen effect by dihydrotestosterone. J Steroid Biochem. 1983; 19(4):1513-20.

57. Westwood F R. The female rat reproductive cycle: a practical histological guide to staging. Toxicol Pathol. 2008; 36(3):375-84.

58. Allan C M, Wang Y, Jimenez M, Marshan B, Spaliviero J, Illingworth P, et al. Follicle-stimulating hormone increases primordial follicle reserve in mature female hypogonadal mice. J Endocrinol. 2006; 188(3):549-57.

59. Cossigny D A, Findlay J K, Drummond A E. The effects of FSH and activin A on follicle development in vitro. Reproduction. 2012; 143(2):221-9.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof) or with respect to other examples (or one or more aspects thereof) shown or described herein.

In the event of inconsistent usages between this document and any documents so incorporated by reference, the usage in this document controls.

The above description is intended to be illustrative and not restrictive. For example, the above-described examples (or one or more aspects thereof) may be used in combination with each other. Other embodiments can be used, such as "by one of ordinary skill in the art" upon reviewing the above description. The Abstract is provided to comply with 37 C.F.R. § 1.72(b) to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in fewer than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims along with the full scope of equivalents to which such claims are entitled.

All publications, patents, and patent applications, Genbank sequences, websites and other published materials referred to throughout the disclosure herein are herein incorporated by reference to the same extent as if each individual publication, patent, or patent application, Genbank sequences, websites and other published materials was specifically and individually indicated to be incorporated by reference. In the event that the definition of a term incorporated by reference conflicts with a term defined herein, this specification shall control.

What is claimed is:

1. A method for preventing the estrous cycle in the female pig or ruminants, which prevents the pubertal development of ovary, ovarian follicles, and production of estrogen until slaughter, comprising administering to said sow or ruminants a combination of an estrogen and androgen within a few weeks or months after birth during the neonatal to infantile period.

2. The method of claim 1, female ruminants include doe, heifer, ewe, and other female livestock.

3. The method of claim 1, wherein the administration is by subcutaneous injection, intra-muscular injection, or by nasal inhalation.

4. The method of claim 1, further comprising an implant wherein the implant comprises said estrogen and androgen.

5. The method of claim 1, wherein the estrogen and androgen target hypothalamus-pituitary axis and ovary development, respectively.

6. The method of claim 4, wherein the implant comprises a material or enclosure that provides sustained release of the compounds over during the neonatal/infantile period.

7. The method of claim 1, wherein the injected estrogen and androgen are not present in the blood or tissues when the animals are slaughtered for meat production.

8. The method of claim 5, wherein the material or enclosure that provides sustained release comprises biodegradable polymers or biocompatible materials.

9. The method of any one of claim 5, wherein the material or enclosure that provides sustained release is a form of capsule, pellets, microspheres, gel, or solution.

10. The method of claim 1, wherein the estrogen comprises estrogenic compounds selected from the group consisting of estradiol benzoate, estradiol valerate, and estradiol cypionate, with a dose range of 0.1-2 mg/kg bodyweight.

11. The method of claim 1, wherein the androgen comprises testosterone, testosterone esters, androstenedione, trenbolone, trenbolone esters, 5α-dihydrotestosterone, 5α-dihydrotestosterone esters, synthetic androgens that has androgenic activity, or equivalents with the dose range of 1-20 mg/kg bodyweight.

12. The method of claim 1, wherein the injected amount of the estrogen/androgen combination is in a dose sufficient to inhibit kisspeptin neurons in the hypothalamus, LH/FSH production in the pituitary, follicle development and production of estrogen in the ovary.

13. The method of claim 8, wherein the material or enclosure comprises silicone.

* * * * *